United States Patent [19]

Leland

[11] 4,242,514
[45] Dec. 30, 1980

[54] METHOD FOR THE INTRODUCTION OF A METHYL GROUP INTO THE 7 POSITION OF THE MORPHINAN NUCLEUS

[75] Inventor: David L. Leland, Elkhart, Ind.

[73] Assignee: Miles Laboratories, Inc., Elkhart, Ind.

[21] Appl. No.: 85,775

[22] Filed: Oct. 17, 1979

[51] Int. Cl.$^3$ .................. C07D 221/28; C07D 489/02
[52] U.S. Cl. ........................................ 546/74; 546/45
[58] Field of Search ................................ 546/74, 45

[56] References Cited

U.S. PATENT DOCUMENTS 2,178,010  10/1939  Small et al. ........................... 546/45

OTHER PUBLICATIONS

Bentley, "The Chemistry of the Morpholine Alkaloids", Oxford University Press, London, (1954), pp. 272-288.
Bentley et al., J. Chem. Soc., pp. 947-957, (1952).
Posner, "Conjugate Addition Reactions of Organocopper Reagents", Organic Reactions, vol. 19, pp. 1-113, (1972).

*Primary Examiner*—Donald G. Daus
*Assistant Examiner*—Diana G. Rivers
*Attorney, Agent, or Firm*—Jerome L. Jeffers

[57] ABSTRACT

Disclosed is a novel method for the introduction of a 7-methyl group into the morphinan nucleus to thereby provide precursors for the preparation of therapeutically useful 7-methyl-4,5α-epoxy morphinan and morphinan-6-one compounds. The method involves reacting thebaine, dihydrothebaine or the enol acetate of dihydrocodeinone with lithium dimethyl cuprate to form the corresponding 7-methyl-4,5α-epoxy cleaved product.

17 Claims, No Drawings

METHOD FOR THE INTRODUCTION OF A METHYL GROUP INTO THE 7 POSITION OF THE MORPHINAN NUCLEUS

BACKGROUND OF THE INVENTION

1. Field of the Invention

The well known narcotic analgesic morphine has the basic ring system:

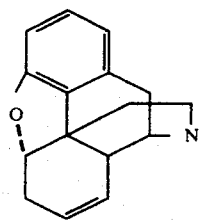

When the oxygen bridge is present and the double bond in the lower ring is removed by saturation, the ring system is referred to as a 4,5α-epoxy morphinan. When the oxygen bridge is not present, the ring system is referred to as the morphinan system, which has the basic structural formula:

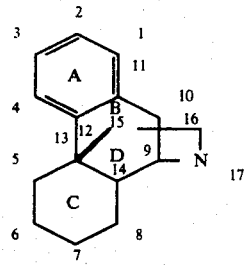

in which the numbering of carbon atoms and ring designations are as indicated. When the hydrogen atom attached to the 14-carbon atom is in the β-configuration, i.e., projecting above the plane of the molecule, the molecule has the same B/C ring junction as the naturally occuring morphine alkanoids and is in the B/C cis configuration. When the 14-hydrogen atom is in the α-configuration, i.e., projecting below the plane of the molecule, it is in the B/C trans configuration.

Morphine and its relatives are used primarily in the relief of pain. They are narcotic and most possess dependence inducing ability and produce other side effects (emesis, constipation, sweating, respiratory depression, miosis) which make them less than ideal analgesics. A compound with an appropriate profile of analgesic (agonist) and narcotic antagonist action has potential as an analgesic free from these side effects. Such a compound would be useful in the treatment of moderate to severe pain, without liability of drug dependence or drug abuse. The search for such an analgesic has led to the synthesis and pharmacological testing of many compounds having the morphinan and 4,5α-epoxy morphinan nucleus. Among those compounds which have demonstrated interesting agonist/antagonist profiles are morphinans which are methoxy or hydroxy substituted at the 3-position, keto substituted at the 6-position and cycloalkylmethyl substituted at the 17-nitrogen. More recently, it has been discovered that the introduction of a methyl group into the 7-position of a 3-methoxy or hydroxy, 6-keto, 17-cycloalkylmethyl morphinan or 4,5α-epoxy morphinan can enhance the pharmaceutical utility of such a compound.

The introduction of a methyl group into the 7-position on the morphinan and 4,5α-epoxy morphinan nucleus has proven difficult and results in only small yields of the desired product. The invention disclosed herein provides a method for the facile introduction of a methyl group, with concurrent 4,5-epoxy bond cleavage, into the 7-position of the morphinan nucleus to thereby provide precursors for therapeutically useful 7-methyl morphinan-6-one compounds.

2. Prior Art

Small et al disclose in U.S. Pat. No. 2,178,010 (issued Oct. 31, 1939) the reaction of dihydrothebaine:

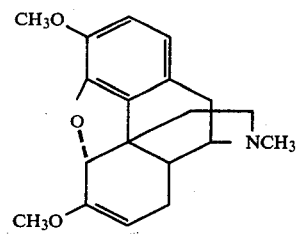

with methylmagnesium iodide in refluxing ether solution for 180 hours to give, after workup which includes acid hydrolysis, a mixture from which may be isolated in 45-58% crude yield (15-17.5% recrystallized) methyldihydrothebainone:

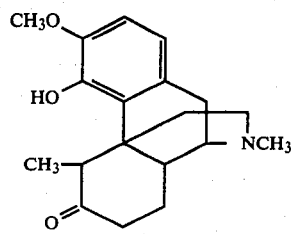

and a 9-11% yield (5-6% recrystallized) of isomethyl dihydrothebainone:

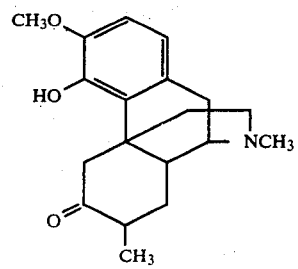

Small et al. also report in J. Org. Chem., 3, 204 (1938) the reaction of dihydrocodeinone enol acetate:

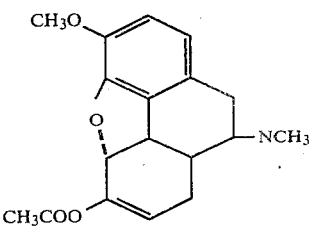

VI

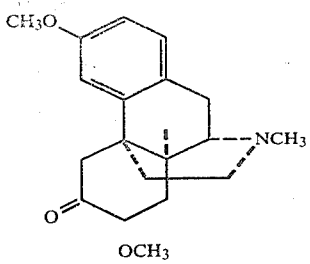

X with methylmagnesium iodide for 24 hours in boiling ether to give a 74% yield of IV and some V with no mention of its exact percent yield. It should be noted that the 7-methyl compound V is the mirror product of these reactions and is difficult to obtain. This is in contrast to the presently reported facile introduction of a methyl group, with concurrent 4,5-epoxy bond cleavage, into the 7-position of the morphinan nucleus.

The introduction of a 7-ketone into the morphinan nucleus with concurrent cleavage of the 4,5-epoxy bond has been reported by Rearick and Gates in Tetrahedron Letters, 507 (1970). They report that treatment of 14-bromocodeinone:

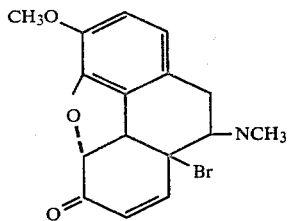

VII with Claisens alkali gives the 7-keto morphinane VIII:

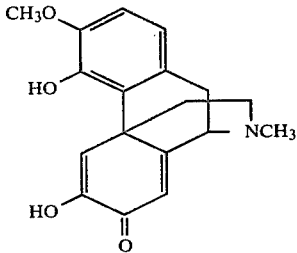

VIII

Sawa et al report the preparation of desoxysinomenine characterized by the formula:

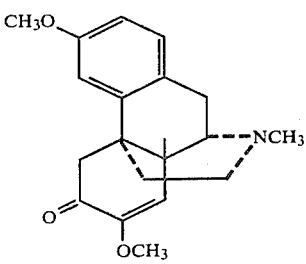

IX and desoxydihydrosinomenine characterized by the formula:

in Tetrahedron, 15, 144 (1961).from the naturally occurring alkaloid, sinomenine:

XI

Introduction of 7-substituents on the 4,5-epoxy morphinan nucleus, without cleavage of the epoxy bond has been reported by several workers. Bentley et al report in Chem. Comm., JCS C, 57 (1969) that nitrosyl chloride reacts with thebaine in methanol to give the dimethyl ketal of 7-hydroxyiminoneopinone. Reaction of thebaine with iodine in the presence of AgNO₂ in methanol-chloroform likewise gives the dimethyl ketal of 7β-iodoneopinone.

Lester et al report in Tetrahedron, 20, 1407 (1964) and 21, 771 (1965) that 14-hydroxy-dihydrocodeinone may be converted to the 7-hydroxyimino derivative by reaction with amylnitrite in chloroform containing ethanolic HCl. This compound can be converted to an ethylene ketal and hydrolyzed to the 7-keto-6-ketal which upon further reaction with dimethylsulphoxonium methylide gives the oxirane.

SUMMARY OF THE INVENTION

The present invention is a method for the introduction of a methyl group into the 7-position of the morphinan nucleus. The method comprises reacting, in an inert solvent, thebaine, dihydrothebaine or the enol acetate of dihydrocodeinone with lithium dimethyl cuprate to form the corresponding 7-methyl 4,5α-epoxy cleaved product.

DETAILED DESCRIPTION AND PREFERRED EMBODIMENTS

General Process Description

The reaction of thebaine, dihydrothebaine or the enol acetate of dihydrocodeinone (starting materials) with lithium dimethyl cuprate is preferably carried out by the use of one to three molar equivalents of the organo copper reagent per mole equivalent of starting material. Ideally this ratio is about 1.25 to 1. For best results the temperature of the reaction mass is maintained at a range of from −30° to +15° C. with a range of from −10° to 0° C. being preferred. The reaction is carried out under an atmosphere of an inert gas such as nitrogen or argon.

The lithium organo copper reagent may be prepared in a lower ether solvent such as diethyl or disopropyl ether or in the cyclic ether, tetrahydrofuran; diethyl ether is preferred. Due to the insolubility of the starting materials in these ether solvents, a different solvent must be used to dissolve these materials prior to addition of the organo copper reagent. Benzene or toluene can be used for this purpose since the starting material is fairly soluble in these aromatic hydrocarbon solvents on warming to above 40° C. It is preferred, however, to use a halogenated hydrocarbon solvent such as methylene chloride, chloroform, trichloroethane or trichloroethylene. Methylene chloride is preferred because of the good solubility of the starting materials in this solvent at room temperature and its volatitity which aids in further processing of the reaction mixture.

The reaction time is typically from five minutes to two hours with a period of from thirty minutes to one hour being preferred. The reaction may be quenched by pouring the reaction mixture into cold dilute aqueous acid or into a saturated solution of ammonia chloride; the latter approach being preferred. After quenching, the reaction mixture is normally adjusted to a pH of between ten and thirteen to insure complete recovery of the alkaloid material. Aqueous solutions of ammonium hydroxide, sodium hydroxide or potassium hydroxide may be utilized in this step; the use of sodium hydroxide to give a pH of about 13 is preferred.

The formation of the 7-methyl-4,5α-epoxy cleaved product by the process of the present invention and the further reaction of this product to form 7-methyl-4,5α-epoxy morphinans useful as mixed analgesics/narcotic antagonists is depicted in Scheme I.

Referring to Scheme I, thebaine (1) is reacted with lithium dimethyl cuprate to provide the 7-methyl-4,5α-epoxy cleaved product, 3,6-dimethoxy-7β,17-dimethyl-4-hydroxy-5,6,8,14-tetradehydromorphinane (2). This compound serves as a useful starting material for the preparation of 7-methyl-3-methoxy-4,5α-epoxy morphinan-6-ones. Thus, to a solution of 1.25 equivalents of lithium dimethyl cuprate, prepared in ether at 0° under inert atmosphere is added a solution of thebaine (1) in benzene or toluene (aromaic hydrocarbon) or methylene chloride (halogenated hydrocarbon) or other suitable inert solvent. The resulting yellow suspension is stirred in the cold for a period of one hour and then poured into a saturated solution of ammonium chloride to quench the reaction. The aqueous phase is adjusted to pH 10 to 13 by use of an inorganic base such as sodium or potassium hydroxide and the organic phase separated. After extraction of the aqueous phase with additional organic solvent, the combined extracts are backwashed, dried and evaporated to a foam. This foam is crystallized from chloroform with the addition of hexane to yield (2) as the monochloroform solvate, mp 98°–101.5°, in about 75% yield.

Compound (2) is hydrolyzed to a mixture of B/C cis and trans 7,8 unsaturated ketones (3). The minor product of this reaction, the B/C trans compound will not undergo the subsequent ring closure necessary to form the final 4,5α-epoxy morphinan and is most conveniently separated from the desired cis isomer at this stage by chromatography. Compound (3) is then reduced to the 7α-methyl derivative (4a) by catalytic means.

As an extention of this method, we have discovered that dihydrothebaine (5), is prepared by the catalytic reduction of thebaine, reacts with lithium dimethyl cuprate under the reaction conditions previously set out, to give as the major product a 7-methyl-4,5α-epoxy cleaved product identified as (6). Mild acid treatment of (6) yields (4a) which may also be obtained from (2) by acid hydrolysis of (3). This route to (4a) eliminates a reaction step in obtaining the 7-methyl-4,5α-epoxy-6-ones but is less preferred because of the low yields obtained in the preparation of dihydrothebaine.

The enol acetate of dihydrocodeinone (7) also reacts with lithium dimethyl cuprate to give a mixture of products which can be resolved by chromatography. These products have been identified as 5,6-didehydro-7,17-dimethyl-4-hydroxy-3-methoxy-morphinane (8), 7β,17-dimethyl-4-hydroxy-3-methoxy-morphinan-6-one (4b) and the corresponding 7α, isomer (4a). Compound (4b) is easily converted to the thermodynamically more stable α-isomer (4a) by acid treatment.

The 17-methyl group of compound (4a) is displaced with a cyano function using an excess of cyanogen bromide. The cyano compound is converted to the nor compound by refluxing in 2N HCl and the nor compound is alkylated using cyclopropylmethyl or cyclobutylmethyl bromide under standard reaction conditions to give compounds of general Formula (9) which, when the 3-methoxy group is converted to 3-hydroxy by treatment with boron tribromide, are useful as mixed analgesics/narcotic antagonists. The conversion of compound (4a) to 7α-methyl-4,5α-epoxy morphinans useful as mixed analgesics/narcotic antagonists is more fully disclosed in co-pending U.S. application Ser. No. 56,549, filed July 11, 1979.

SCHEME I

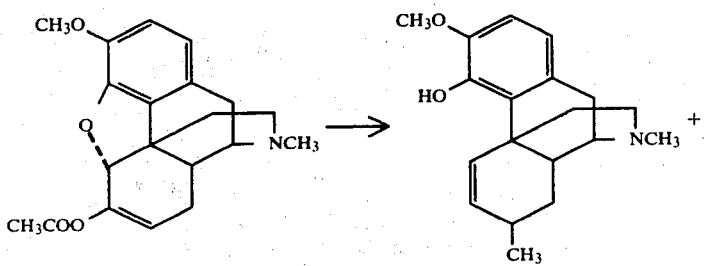

7 8

-continued
SCHEME I

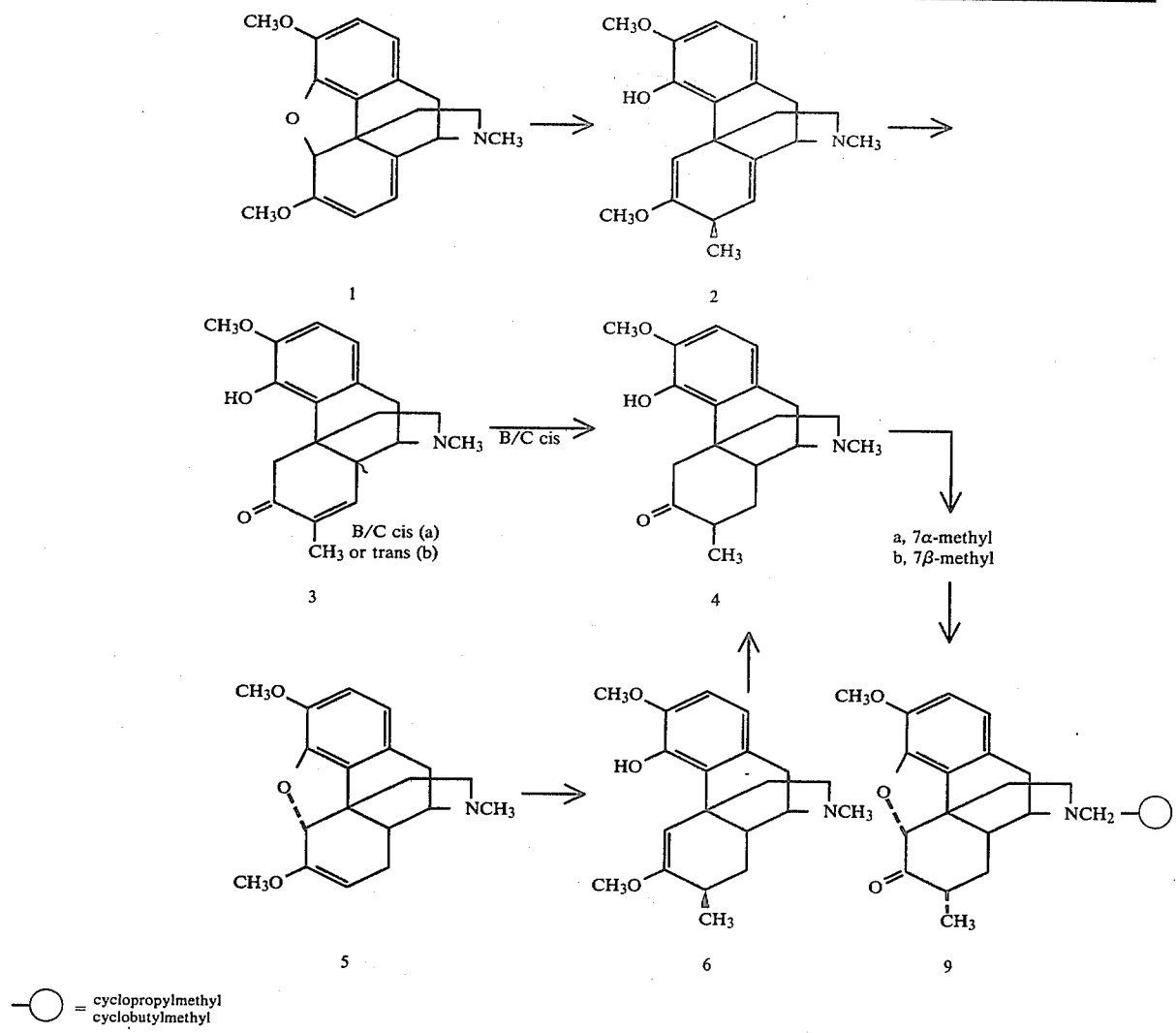

The conversion of key intermediate (2), formed by the process of the present invention as outlined above, to therapeuticaly useful 7α-methyl-morphinan-6-one compounds is illustrated by Scheme II.

Referring to Scheme II, compound (2) 3,6-dimethyoxy-7β,17-dimethyl-4-hydroxy-5,6,8,14-tetrahydromorphinane, isolated as the crystalline chloroform solvate is converted to the 4-phenyl ether (10) by reaction with bromobenzene in refluxing pyridine in the presence of an acid acceptor and copper powder. The 4-phenoxy group is cleaved from (10) to give (11) by use of sodium in a liquid ammonia-toluene mixture. Acid hydrolysis of (11) by use of 90% acetic acid at 95° C. for twenty to thirty minutes gives a mixture of the isomeric B/C cis and trans ketones (12) which are most conveniently separated at this point by chromatography. Each isomer is then individually carried through the remainder of the reaction sequence although for purposes of Scheme II, the B/C cis and trans isomers are treated as a single compound. Compound (12) is treated with hydrogen over a palladium-charcoal catalyst in acidified ethanol solution to reduce the double bond in the 7,8 position and provide compound (13). In the B/C cis series, the hydrogen is added from the β-face of the molecule with the result that the 7-methyl group in (13a) occupies the α-position. In the B/C trans series, which results in (13b), we believe the 7-methyl group occupies the β-position. Replacement of the 17-methyl group with a cycloalkylmethy via the cyano and nor compound as previously described provides 7α or β-methyl, 17-cyclopropylmethyl or cyclobutylmethyl-6-one morphinans (14) useful as mixed analgesics/narcotic antagonists. The preparation of these compounds from intermediate (2) is more fully described in copending U.S. application Ser. No. 40,664 filed May 21, 1979.

SCHEME II

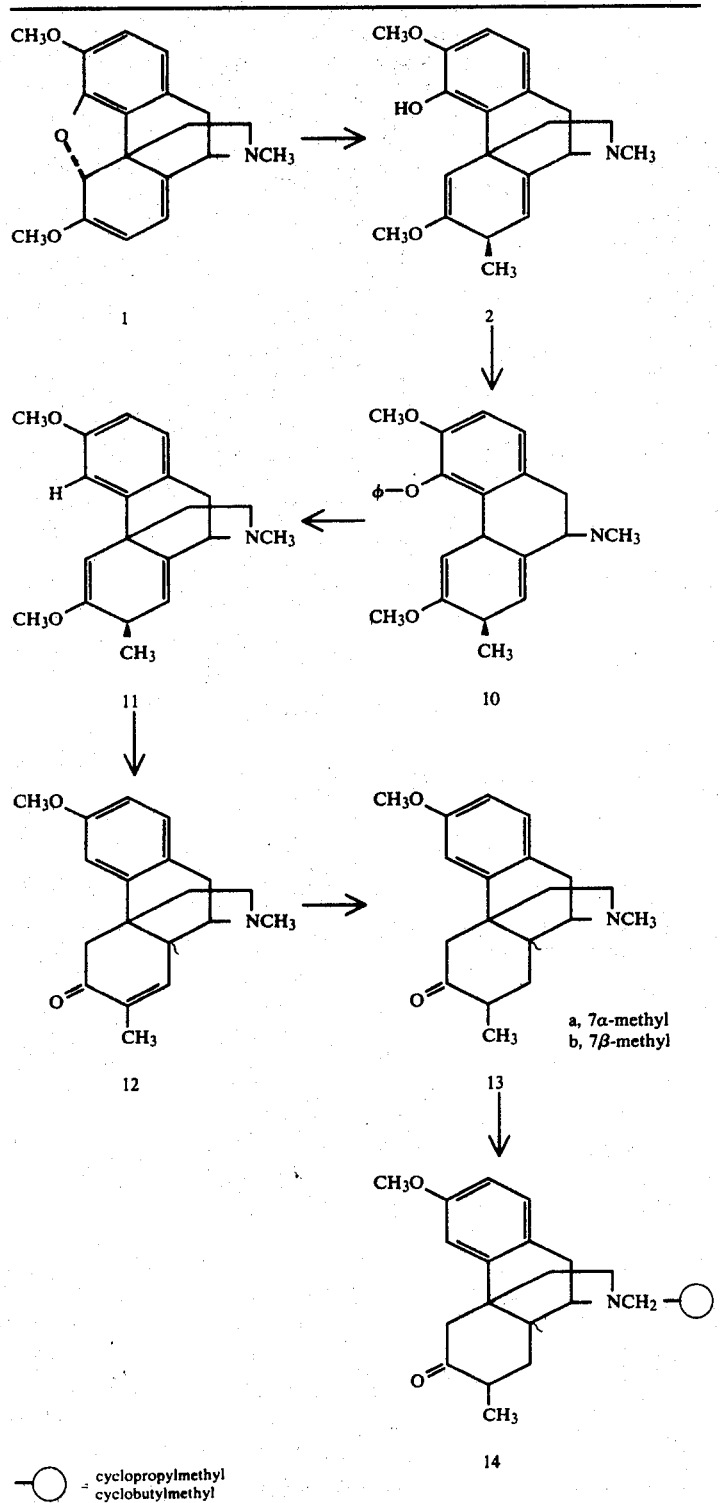

◯ = cyclopropylmethyl
    cyclobutylmethyl

The method for the preparation of key intermediates in the production of 7-methyl-4,5α-epoxy morphinan and morphinan-6-one compounds which method is the subject matter of this invention, is further illustrated by the following examples where the numerical designations for particular compounds correspond with those of Scheme I and II.

EXAMPLE I 3,6-Dimethoxy-7β,17-dimethyl-4-hydroxy-5,6,8,14-tetradehydromorphinane (2)

To a solution of lithium dimethyl cuprate, prepared from copper iodide (23.81 g, 125 mmole) and methyl lithium (250 mmole, 136 ml of a 1.8 M solution in ether containing lithium bromide), in ether (500 ml) stirred in an ice-salt bath under an argon atmosphere, was added rapidly in a thin stream a solution of thebaine (1, 31.14 g, 100 mmole) in benzene (500 ml). The resulting suspension was stirred for 1 hour in the cold, poured into saturated NH$_4$Cl solution (600 ml) and stirred for 15 minutes. The organic layer was separated and the aqueous phase adjusted to pH 13–14 by use of 50% NaOH solution. The aqueous phase was extracted with two portions of chloroform, the combined organic phases were washed with dilute ammonium hydroxide and dried. Evaporation of the organic phase gave a foam which crystallized from chloroform with the addition of hexane to give 33.20 g (74% theory of (2)) as the monochloroform solvate, mp 97°–100°. Recrystallization from the same solvent pair gave analytically pure (2.CHCl$_3$), mp 98°–101.5°. IR (CDCl$_3$): 3500 cm$^{-1}$ (OH). NMR (CDCl$_3$): δ7.30, s (1), CHCl$_3$; 6.65, m (2), H1 and H2; 6.13, s (1), H5; 5.47, d (1), H8, J 7,8=3 Hz; 3.86, s (3), 3—OCH$_3$; 3.63, s(3), 6—-OCH$_3$; 2.33, s(3), 17—NCH$_3$; 1.17, d(3), 7—CH$_3$, J 7H,7CH$_3$=7 Hz; exchangeable, 4—OH at ~6.20.

Anal. Calc. for C$_{20}$H$_{25}$NO$_3$·CHCl$_3$: C, 56.46; H, 5.87; N, 3.13. Found: C, 56.27; H, 5.82; N, 3.07.

EXAMPLE II

A.
7,8-Didehydro-7,17-dimethyl-4-hydroxy-3-methoxymorphinan-6-one (3)

Lithium dimethyl cuprate was prepared in ether (1 liter) under an argon atmosphere below 0° from copper iodide (95.2 g, 0.5 mole) and methyl lithium (1 mole in ether). To this was added, in a thin stream, a solution of thebaine (1, 124.6 g, 0.4 mole) in methylene chloride (900 ml). The mixture was stirred below 0° for 15 minutes and then allowed to warm to room temperature. Saturated NH$_4$Cl solution (1 liter) was added followed by concentrated NH$_4$OH (150 ml). After stirring for 30 minutes, the organic phase was separated and washed twice with dilute NH$_4$OH solution. The aqueous phase was extracted twice with methylene chloride and the combined organic phases dried and evaporated to give a foam which contained predominantly compound (2) 3,6-dimethoxy-7β,17-dimethyl-4-hydroxy-5,6,8,14-tetradehydromorphinane.

The foam containing (2) was heated at 95° with 90% aqueous acetic acid (500 ml) for 30 minutes. The mixture was cooled in ice and then poured into concentrated NH$_4$OH (1 liter). This basic solution was extracted with three portions of chloroform, the organic extracts backwashed twice with dilute NH$_4$OH, and the organic phase dried and evaporated to a thick syrup. The syrup was fractionated by filtration through a settled slurry of Silica Gel G (400 g), packed in a large sintered glass Buchner funnel using 30:1 methanol-chloroform as the suspending media and eluting solvent. Early fractions contained a mixture of (3a) and the corresponding B/C trans isomer (3b). Later fractions consisting mainly of (3a) were pooled and evaporated to give 94 g of a foam. The foam was crystallized from ethyl acetate to give 31 g (25%) of compound (3a). Recrystallization from ethyl acetate gave white needles of the hemi-ethyl acetate solvate of (3a), m.p. 183°–185.5°. NMR (CDCl$_3$): δ 6.58 (2H), aromatic; 6.40 broad s (2H), H-8 and —OH; 4.30, d (1H), H-5α, J=15 Hz; 3.76, s (3H), CH$_3$O; 2.40, s(3H), CH$_3$N—; 1.60, m (3H), 7 CH$_3$—.

B.
7α,17-Dimethyl-4-hydroxy-3-methoxymorphinan-6-one (4)

To a solution of (3a) (22.0 g, 70 mmole) in 95% ethanol (200 ml) was added concentrated HCl (12 ml) and 10% palladium on activated carbon (2.0 g). The mixture was hydrogenated at an initial pressure of 50 psi until the uptake of hydrogen ceased. The mixture was filtered from the catalyst and the filtrate evaporated to a small volume. The residue was dissolved in water, the solution made basic with concentrated NH$_4$OH and extracted with three portions of chloroform. The chloroform extracts were washed with dilute NH$_4$OH, dried and evaporated to a thick syrup which crystallized on the addition of ethyl acetate. The crystals were collected and dried to give 14.4 g (65%) of (4a) as white needles, mp 163°–165°. Recrystallization from acetone gave analytically pure (4a) as the hemi-acetone solvate, mp 166°–167°. NMR (CDCl$_3$): δ 6.55, s(2H), aromatic; 6.40, broad (1H), hydroxyl; 4.22, d(1H), H-5α, J=13 Hz; 3.77, CH$_3$O; 2.38, CH$_3$N—; 0.87, d(3H), 7α CH$_3$—, J=6.5 Hz. [α]$_D$= −55° (c=1.00, CHCl$_3$).

Anal. Calc. for C$_{19}$H$_{25}$NO$_3$·0.5 C$_3$H$_6$O: C, 71.48; H, 8.19; N, 4.07. Found: C, 71.69; H, 8.27; N, 4.12.

EXAMPLE III

A.
5,6-Didehydro-3,6dimethoxy-7β,17-dimethyl-4-hydroxymorphinane (6)

A solution of lithium dimethyl cuprate was prepared in ether (60 ml) at 0° under an argon atmosphere from copper iodide (2.38 g, 12.5 mmole) and ethereal methyl lithium (25 mmole, 14 ml of a 1.84 M solution). To this was added rapidly dropwise a solution of dihydrothebaine (5, 3.13 g, 10 mmole) in benzene (75 ml) and the reaction mixture stirred in the ice bath for one hour. The mixture was then poured into saturated NH$_4$Cl solution and stirred for 30 minutes. The solution was adjusted to about pH 11 with concentrated NH$_4$OH and the organic phase separated. The aqueous phase was extracted with several portions of chloroform, the combined organic phases backwashed with dilute NH$_4$OH and then dried, filtered and evaporated to give 3.76 g of a foam. This foam was chromatographed over Silica Gel G (400 g) using 10:1 chloroform-methanol containing 1% concentrated NH$_4$OH as the eluant. Fractions containing the major product, which were homogeneous by thin layer chromatography were combined and evaporated to give 2.54 g (77%) of (6) as a foam. NMR (CDCl$_3$): δ 6.60, s(2H), aromatic H's; 6.13, broad (1H), hydroxyl H; 5.68, s(1H), H-5; 3.83, 3 CH$_3$O—; 3.58, 6 CH$_3$O—; 2.40, CH$_3$N—; 1.18, multiplet, 3H, 7 CH$_3$—.

B.
7α,17-Dimethyl-4-hydroxy-3-methoxymorphinan-6-one (4a)

A solution of (6) (2.54 g, 7.7 mmole) in 1 N HCl (30 ml) was heated on the steam bath for 30 minutes. The cooled solution was made basic with concentrated NH$_4$OH and extracted with three portions of chloroform. The chloroform extracts were evaporated to give a crystalline residue. The residue was dissolved in hot acetone and cooled. Crystals (1.29 g) of the hemi-acetone solvate of (4a) were collected after cooling. Recrystallization from acetone gave analytically pure (4a)

as hemi-acetone solvate, mp 166°–167°, identical with material prepared previously.

EXAMPLE IV
Reaction of dihydrocodeinone enol acetate (7) with lithium dimethyl cuprate A solution of dihydrocodeinone enol acetate (7, 6.40 g, 20 mmole) in benzene (100 ml) was added rapidly dropwise to a solution of lithium dimethyl cuprate (40 mmole) prepared in ether (200 ml) at 0° under an argon atmosphere. The reaction mixture was stirred for 1 hour at 0° and then poured into saturated NH$_4$Cl solution. The mixture was adjusted to pH~10 with concentrated NH$_4$OH and then stirred for 30 minutes and processed as described above for (4). The organic phases were evaporated to a foam which contained four major spots by thin layer chromatography. This foam was chromatographed over Silica Gel G (750 g) using 15:1 chloroform-methanol containing 0.75% concentrated NH$_4$OH as the eluant. Fractions were combined on the basis of thin layer chromatography.

The first major fraction eluted weighed 1.48 g. This material was identified as 5,6-didehydro-7,17-dimethyl-4-hydroxy-3-methoxymorphinane (8). NMR (CDCl$_3$): δ6.63, s (2.5), aromatic and ½ doublet for H-5; 6.46, ½ unsymmetrical d for H-5; 6.00, hydroxyl H; 5.55, pair of doublets (1), H-6, J 5,6=10 Hz, J 6,7=3.5 Hz; 3.83, s (3), CH$_3$O; 2.40, s (3), CH$_3$N—; 1.05, unsymmetrical d (3), J=7 Hz, 7 CH$_3$—. This material was converted to the HCL salt, mp dec. above 250°, which was crystallized from ethyl acetate for analysis.

Anal. Calcd. for C$_{19}$H$_{25}$NO$_2$.HCl: C, 67.94; H, 7.80; N, 4.17. Found: C, 67.70, H, 7.89; N, 4.07.

The second major fraction eluted weighed 1.71 g and was identified as 7β,17-dimethyl-4-hydroxy-3-methoxymorphinan-6-one (4b). NMR (CDCl$_3$): δ6.62, aromatic; 4.10, H-5α, J=15 Hz; 3.82, CH$_3$O—, 2.43, CH$_3$N—; 1.21, d, 7βCH$_3$—, J=7 Hz. This material was crystallized and recrystallized from ethyl acetate to give the hemi-ethyl acetate solvate of (4b), mp 163°–165°. [α]$_D$=−115° (C=1.02, CHCl$_3$).

Anal. Calcd. for C$_{19}$H$_{25}$NO$_3$.0.5 C$_4$H$_8$O$_2$: C, 70.17; H, 8.13; N, 3.90 Found: C, 70.44; H, 8.19; N, 3.87.

Compounds (2) and (4) are converted to therapeutically useful 7-methyl-morphinan-6-one and 7-methyl-4,5α-epoxymorphinan-6-one compounds as previously described in the textual description of Schemes I and II.

What is claimed is:

1. A method for the introduction of a methyl group into the 7-position of the morphinan nucleus which method comprises reacting, in an inert solvent under an inert atmosphere, thebaine with lithium dimethyl cuprate for a time sufficient to form 3,6-dimethoxy-7β,17-dimethyl-4-hydroxy-5,6,8,14-tetrahydromorphinane.

2. The method of claim 1 wherein one to three molar equivalents of the organo copper reagent per mole equivalent of thebaine is employed.

3. The method of claim 2 wherein the ratio is about 1.25 to 1.

4. The method of claim 1 wherein the reaction temperature is maintained at a range of from −30° to 15° C.

5. The method of claim 1 wherein the reaction temperature is maintained at a range of from −10° to 0° C.

6. The method of claim 1 wherein the inert atmosphere is nitrogen or argon.

7. The method of claim 1 wherein the inert solvent is an aromatic hydrocarbon.

8. The method of claim 7 wherein the aromatic hydrocarbon is benzene or toluene.

9. The method of claim 1 wherein the inert solvent is a halogenated hydrocarbon.

10. The method of claim 9 wherein the halogenated hydrocarbon is methylene chloride, chloroform, trichloroethane or trichloroethylene.

11. The method of claim 10 wherein the halogenated hydrocarbon is methylene chloride.

12. The method of claim 1 wherein the reaction is carried out for a time of from five minutes to two hours.

13. The method of claim 12 wherein the time is from thirty minutes to one hour.

14. The method of claim 1 wherein, after formation of the desired product, the reaction is quenched by combining the reaction mixture with cold dilute aqueous acid or a saturated solution of ammonium chloride and the pH is adjusted to a value of between 10 and 13 by the addition of an aqueous solution of ammonium hydroxide or potassium hydroxide.

15. The method of claim 14 wherein the pH is adjusted to a level of about 13 by the addition of sodium hydroxide.

16. A method for the preparation of 3,6-dimethoxy-7β,17-dimethyl-4-hydroxy-5,6,8,14-tetradehydromorphinane which comprises reacting, in methylene chloride, thebaine with lithium dimethyl cuprate at a temperature of from −30° to 15° C. for a time of from five minutes to two hours.

17. The method of claim 16 wherein the temperature is from −10° to 0° C. and the time is from thirty minutes to one hour.

* * * * *